(12) United States Patent
Jouvin

(10) Patent No.: US 7,300,422 B2
(45) Date of Patent: Nov. 27, 2007

(54) PROTECTIVE SHEATH FOR A CANNULA, INJECTION UNIT COMPRISING SUCH A SHEATH AND NEEDLE PROVIDED WITH SUCH A SHEATH

(76) Inventor: Jean Luc Jouvin, 6, boulevard Oyon, Le Mans (FR) F-2000

( * ) Notice: Subject to any disclaimer, the term of this patent is extended or adjusted under 35 U.S.C. 154(b) by 0 days.

(21) Appl. No.: 10/548,628

(22) PCT Filed: Mar. 11, 2004

(86) PCT No.: PCT/FR2004/000585
§ 371 (c)(1),
(2), (4) Date: Feb. 9, 2006

(87) PCT Pub. No.: WO2004/082730
PCT Pub. Date: Sep. 30, 2004

(65) Prior Publication Data
US 2006/0184113 A1 Aug. 17, 2006

(30) Foreign Application Priority Data
Mar. 11, 2003 (FR) .................................. 03 03007

(51) Int. Cl.
*A61M 5/32* (2006.01)
(52) U.S. Cl. ...................................... 604/198; 604/110

(58) Field of Classification Search ................ 604/110, 604/192, 198, 197, 187
See application file for complete search history.

(56) References Cited

U.S. PATENT DOCUMENTS

| 4,813,940 | A | * | 3/1989 | Parry ........................ 604/198 |
| 5,201,721 | A | | 4/1993 | Lee et al. |
| 5,554,122 | A | | 9/1996 | Emanuel |
| 6,527,742 | B1 | | 3/2003 | Malenchek |

FOREIGN PATENT DOCUMENTS

| FR | 2 716 113 | | 8/1995 |
| WO | WO 95/21545 | * | 8/1995 |
| WO | WO 95/21646 | * | 8/1995 |

* cited by examiner

*Primary Examiner*—Kevin C. Sirmons
*Assistant Examiner*—Catherine N. Witczak
(74) *Attorney, Agent, or Firm*—Buchanan, Ingersoll & Rooney, PC

(57) ABSTRACT

The present invention relates to a protective sheath for an injection needle or cannula arranged on a cannula-holding support, said sheath comprising guide means making it possible at least to move said cannula holder from a completely retracted position to an ejection position, further comprising preliminary locking means enabling said cannula holder to be temporarily locked in a retracted pre-use position. The invention also relates to an injection unit and to a needle equipped with a sheath.

12 Claims, 5 Drawing Sheets

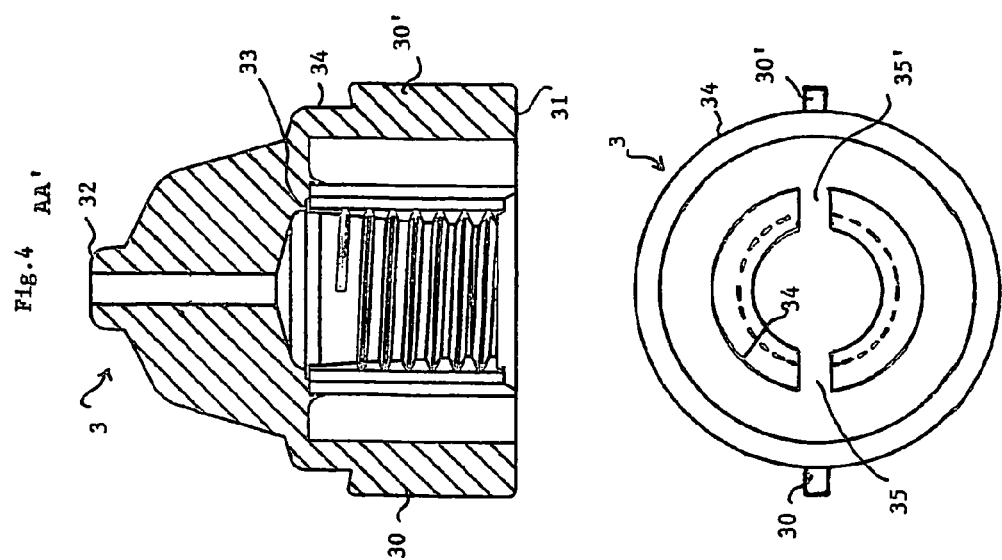
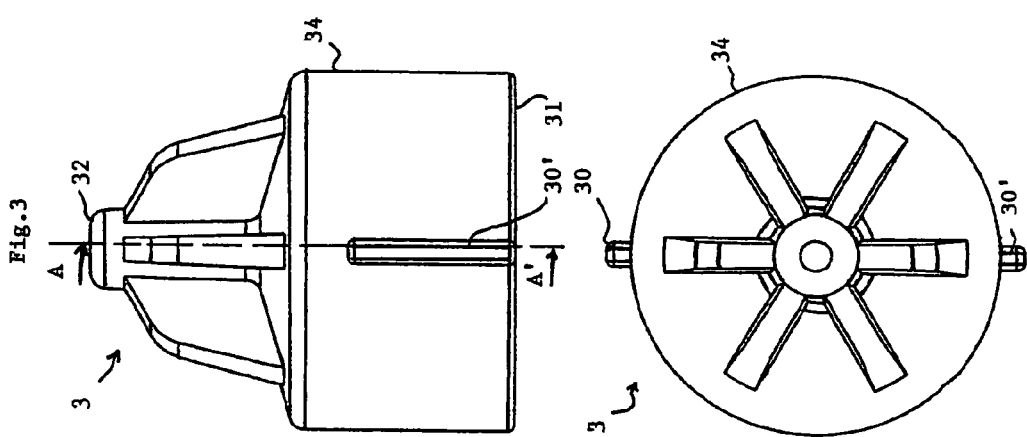
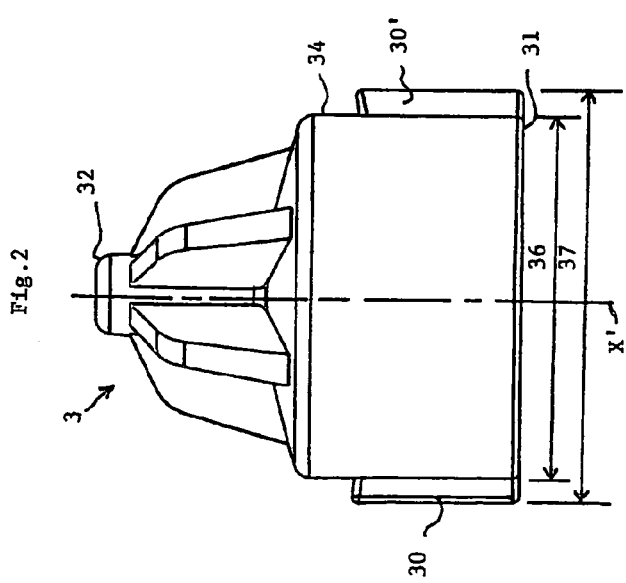

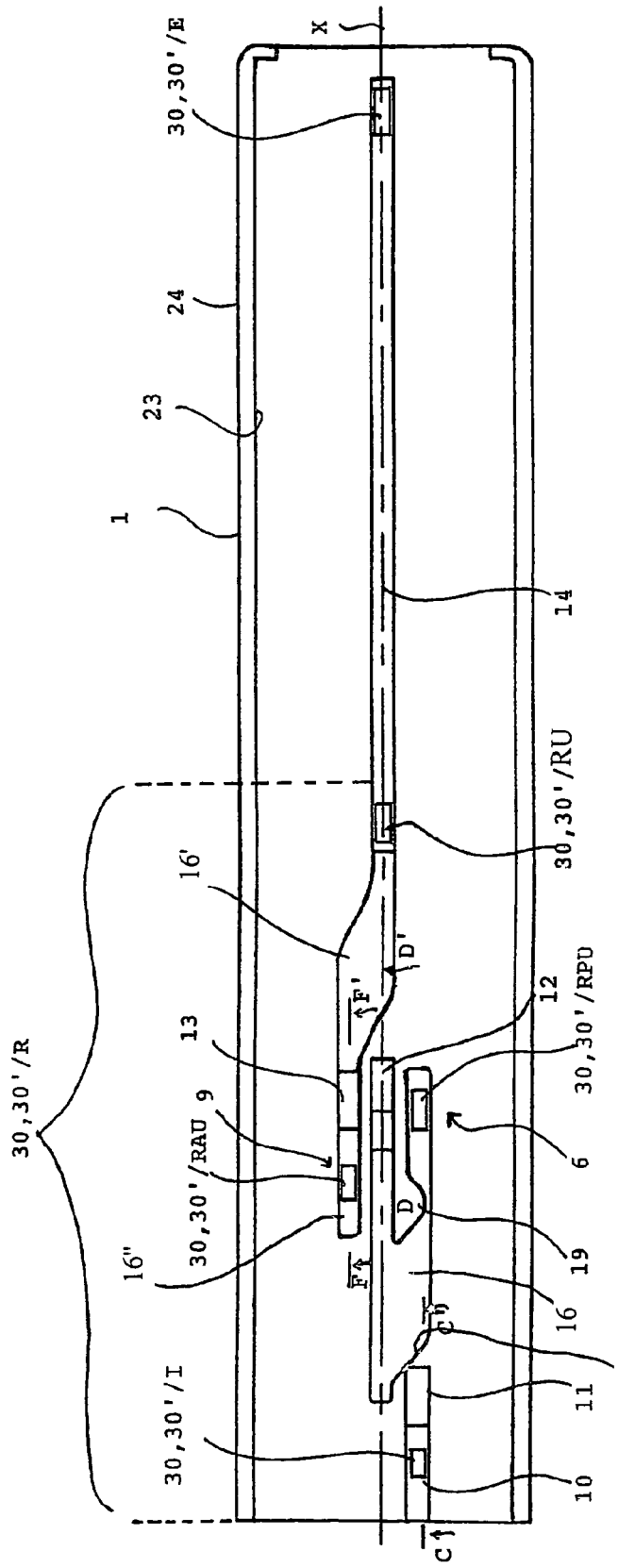
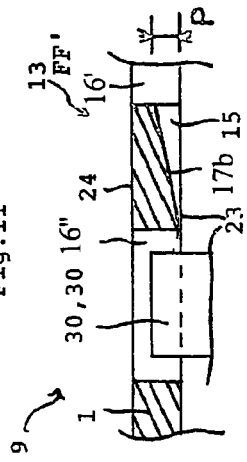
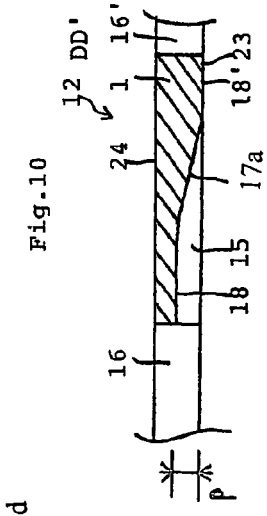

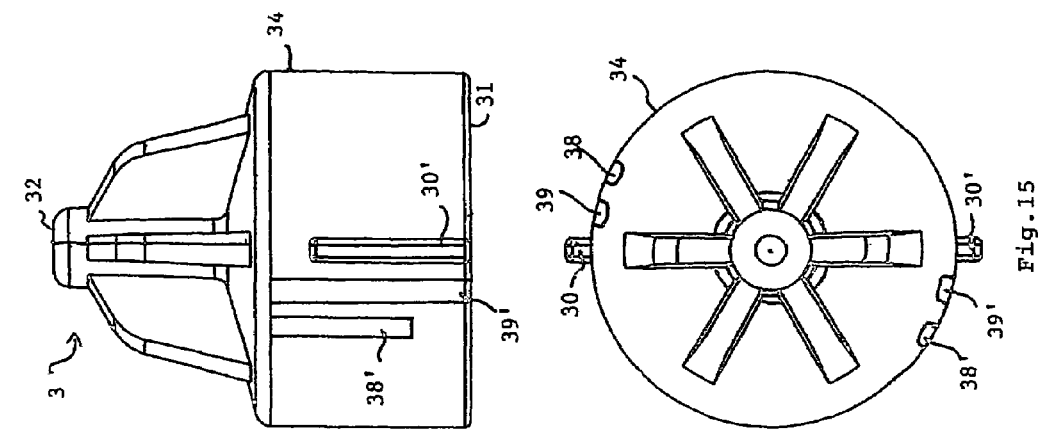
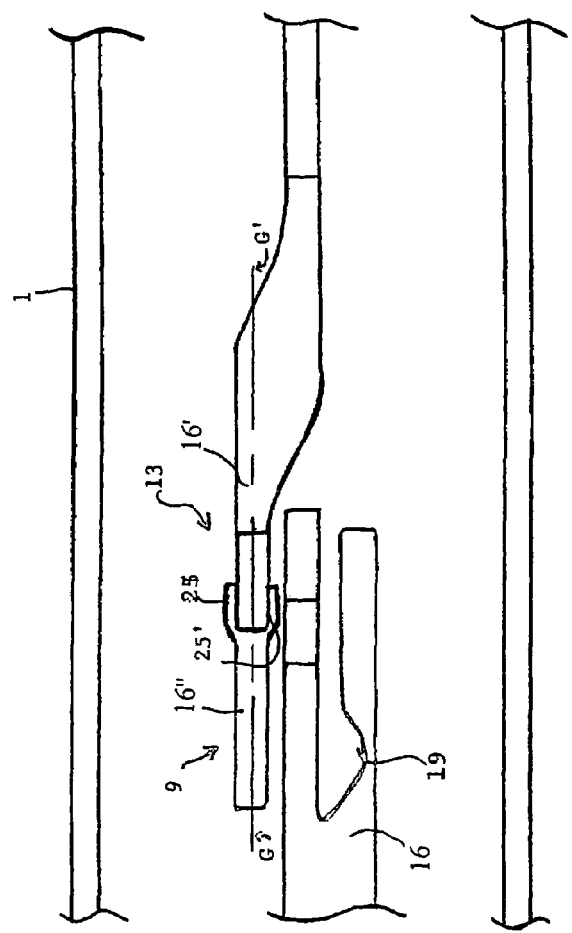
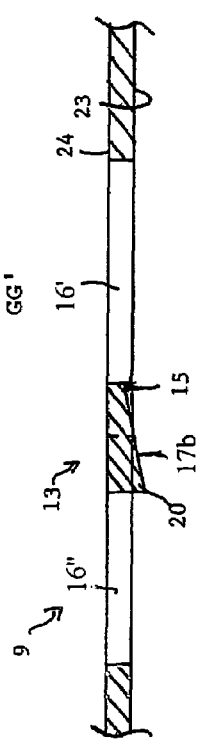

PROTECTIVE SHEATH FOR A CANNULA, INJECTION UNIT COMPRISING SUCH A SHEATH AND NEEDLE PROVIDED WITH SUCH A SHEATH

This is the National Stage of International Application No. PCT/FR04/00585 filed Mar. 11, 2004 which claims priority from French Application No. FR03/03007 filed Mar. 11, 2003.

The present invention relates to the field of protective devices for syringes and, in particular, for syringes for dental use.

The present invention relates more specifically to a protective sheath for an injection needle or cannula arranged on a cannula-holding support which can be fitted onto a syringe, said sheath comprising guide means making it possible at least to move said cannula holder from a completely retracted position, in which said cannula is completely inside said sheath, to an ejection position in which said cannula projects at least partially outside said sheath, and vice versa, said sheath also comprising final locking means enabling said cannula holder to be permanently locked in a retracted post-use position.

The prior art already discloses protective sheaths for cannulas arranged on cannula-holding supports which can be fitted onto syringes.

U.S. Pat. No. 4,772,272 proposes a protective sleeve for a disposable or non-disposable syringe.

The object of that invention is to simplify the movements of the sleeve with respect to the cannula support so that the protective sleeve does not need to be rotated but only to be moved translationally to release or cover the cannula.

The sleeve is provided with first means enabling the sleeve to be retained reversibly in the retracted-needle position and second means enabling the sleeve to be retained reversibly in the extended-needle position.

The first means are formed by an additional cap, but this solution generates extra manufacturing cost and does not display the required reliability. If the practitioner exerts excessive force, the needle may come out and prick him.

Furthermore, this solution does not make it possible to permanently lock the sleeve in a position in which the cannula is protected after use.

The present invention intends to overcome the disadvantages of the prior art by providing a protective device for a cannula which can be fitted onto a non-disposable syringe, which is simple to manufacture and to use, is inexpensive, enables the cannula to be attached to the syringe without risk of the cannula coming out during this operation, and features a final protective position in which it is no longer possible to bring out the cannula.

To this end, the present invention is of the type described above and it is noteworthy, in its broadest sense, in that the sheath additionally comprises preliminary locking means enabling said cannula holder to be temporarily locked in a retracted pre-use position.

The sheath preferably comprises:
primary transition means enabling the cannula holder to be brought into the retracted pre-use position;
secondary transition means enabling the cannula holder to be brought from the retracted pre-use position to a retracted use position;
tertiary transition means enabling the cannula holder to be brought from a retracted use position to a retracted post-use position.

Said primary, secondary and tertiary transition means are preferably single-transition means, that is to say that the single means or plural means allows or allow only a single passage from a particular position to another particular position.

Said primary transition means and/or said secondary transition means and/or said tertiary transition means are each preferably formed at least by a transition portion having, in longitudinal section, a recess made in the inner face of said sheath, said single or said plural transition means having, at each of its or of their ends, a hole and, between these holes, an inclined flat section progressively taking the depth p of said recess toward a zero, or even negative, value.

Said transition portion preferably additionally comprises, in longitudinal section, a straight flat section between the inclined flat section and the hole.

In one variant, the hole situated in the vicinity of the zero, or even negative, depth p is extended at least partially on each side of the inclined plane by longitudinal slots.

In another variant, said primary and/or secondary and/or tertiary transition means are each formed by a transition portion formed by a lug, this lug preferably being oriented radially.

The sheath preferably comprises at its proximal end receiving means enabling said cannula holder to be positioned in an introduction position.

The receiving means and/or said guide means are preferably formed at least by a longitudinally slit portion opening at least onto the internal face of said sheath.

Said primary transition means and/or said secondary transition means and/or said tertiary transition means and/or said guide means are preferably formed by two identical portions positioned diametrically opposite one another about an axis of said sheath Said preliminary locking means are preferably formed by a lug, this lug preferably being oriented radially.

In a preferred version, said sheath comprises a pawl extending toward the inside of said sheath, and said cannula holder comprises at least one primary longitudinal slot and at least one secondary longitudinal slot which are intended to cooperate with said pawl.

The present invention also relates to an injection unit formed by a sheath according to the invention, into which an injection needle or cannula arranged on a cannula-holding support is introduced.

Said cannula holder preferably has at least two longitudinal bosses positioned diametrically opposite one another with respect to the axis of said cannula holder.

The present invention also relates to a syringe comprising an injection needle or cannula, said syringe being equipped with a sheath according to the invention.

Advantageously, the present invention features a position, namely the retracted pre-use position, which makes it possible to clip, or possibly screw, the distal end of the syringe onto the cannula holder in complete safety without risking ejection of the cannula during this operation.

When the injection unit is marketed with the cannula holder in the retracted pre-use position, the cannula (2) is unable to accidentally come out of the sheath toward the proximal end or toward the distal end of the sheath since the preliminary locking means prevents it from doing so.

In order to be able to use the cannula as a needle, the cannula holder must be deliberately withdrawn toward the proximal end of the sheath and then the cannula holder must be pushed toward the distal end of the sheath to activate the secondary transition means. The cannula holder then arrives in the retracted use position and can be pushed in the guide means to bring out the cannula. As long as the tertiary transition means is not crossed, the cannula may be retracted into the sheath or brought out of the sheath as many times as desired.

Advantageously too, the present invention features a position, namely the retracted post-use position, in which it is no longer possible to eject the cannula. In this position, the sheath wall opposes any advancing movement of the cannula holder toward the distal end of the sheath, and slots made laterally in the female region of the thread used to attach the cannula holder to the distal end of the syringe cause the cannula holder and the syringe to be detached when the cannula holder is pulled toward the proximal end of the sheath.

In this retracted post-use position the cannula can therefore not be reused.

The invention will be better understood with the aid of the purely explanatory description given hereinbelow of an embodiment of the invention, with reference to the appended figures:

FIG. 2 illustrates a front view of a cannula holder;

FIG. 3 illustrates a front view of the cannula holder of FIG. 2 turned through 90° with respect to its longitudinal axis;

FIG. 4 illustrates a view in longitudinal section taken along AA' of FIG. 3;

FIG. 5 illustrates a top view of a cannula holder;

FIG. 6 illustrates a bottom view of a cannula holder;

FIG. 8 illustrates a front view of the sheath and of the various positions of the bosses of the cannula holder;

FIG. 10 illustrates a view in longitudinal section taken along DD' of FIG. 8;

FIG. 11 illustrates a view in longitudinal section taken along FF' of FIG. 8;

FIG. 12 is an enlarged partial front view of a variant embodiment of the tertiary transition means;

FIG. 13 is a view in section taken along GG' of FIG. 12;

FIG. 14 illustrates a front view of the cannula holder in the case of the variant of FIG. 12; and FIG. 15 illustrates a top view of a cannula holder of FIG. 14.

Figure 1:
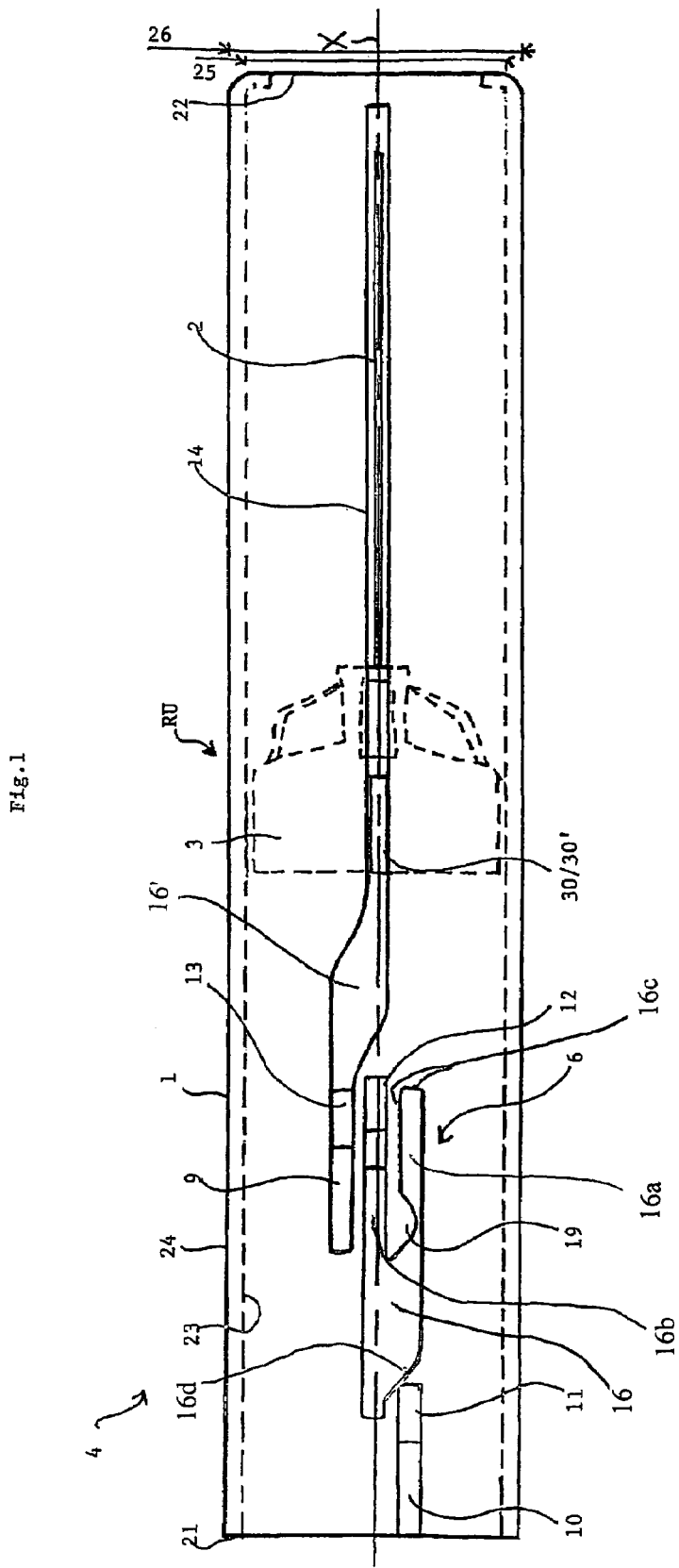
FIG. 1 illustrates a front view of an injection unit according to the invention, composed of a sheath, of a cannula and of a cannula holder.

A dental syringe for the injection, for example, of a local anesthetic may be equipped with a sheath (1), as illustrated in FIG. 1, protecting an injection needle or cannula (2), arranged on a cannula-holding support (3), as illustrated in FIGS. 2 to 6. The sheath (1), the cannula (2) and the cannula holder (3) thus form an injection unit (4).

The injection unit (4) according to the invention is formed only by the sheath (1) and by the cannula holder (3) supporting the cannula (2). No other piece besides the sheath (1) is provided for the protection of the cannula (2).

The sheath (1) has the general shape of a cylindrical tube having a longitudinal axis X. The sheath is open at its proximal (21) and distal (22) ends. It is made of transparent plastic, for example, and has a substantially constant thickness over its entire length. However, to save on material, it is possible to reduce the thickness of the sheath (1) in the parts which do not include any particular protective means, i.e. in the top and bottom parts with regard to FIG. 1.

The sheath (1) has an inner face (23) and an outer face (24) with respect to the axis X. It also has an inside diameter (25) and an outside diameter (26).

The cannula holder (3) is intended to be positioned temporarily at the distal end of the syringe. It provides fluid communication between the cartridge containing the liquid to be injected and the cannula (2).

The cannula holder (3) has the general shape of a cylindrical tube having a longitudinal axis X'. The cannula holder (3) is open at its proximal end (31) and is closed at its distal end (32) over the cannula (2) or over a cylindrical cavity for the reception of the cannula, as visible in FIG. 4. It also has an inner face (33) and an outer face (34) with respect to the axis X'.

The inner face (33) is preferably provided with a thread so as to make it possible for the cannula holder (3) to be clipped, or even screwed, onto the syringe. This thread is preferably interrupted by two longitudinal slots (35, 35'), as can be seen in FIG. 6, so as to allow clipping-on to be effected by the parting movement of two threaded portions, each forming a jaw, when positioning the cannula holder on the thread of the distal end of the syringe.

The cannula holder (3) also has an outside diameter (36), which is slightly smaller than the inside diameter (25) of the sheath (1).

The cannula holder (3) additionally comprises at least one and preferably two bosses (30, 30') positioned diametrically opposite one another with respect to the axis X'. In the region of these bosses, the cannula holder (3) has an overall width (37) which is greater than the inside diameter (25) of the sheath (1) and substantially identical to, or even slightly smaller than, the outside diameter (26) of the sheath (1).

The distal end of the bosses (30, 30') is preferably not perpendicular to the axis X' but inclined toward the proximal end of the cannula holder (3).

The cannula holder (3) is intended to be introduced through the proximal end (21) of the sheath (1) in such a way that the respective axes X and X' of the sheath and of the cannula holder (3) coincide.

Figure 7:
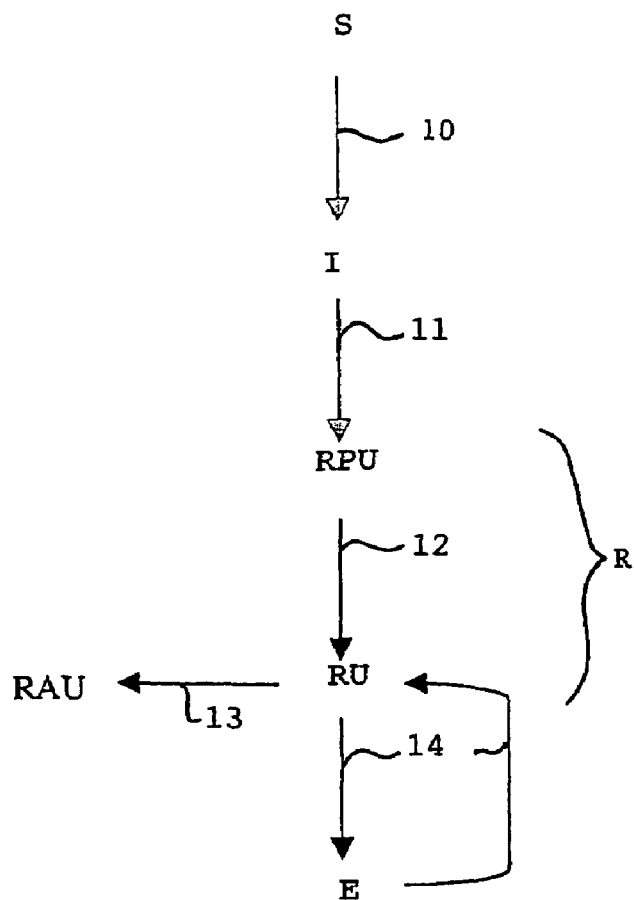
FIG. 7 illustrates the flow diagram of the various positions of the cannula holder in relation to the sheath.

The injection unit (4) formed by the cannula (2) and said cannula holder (3) on the one hand and by the sheath (1) on the other hand features a plurality of positions, as illustrated schematically in FIG. 7:

- a separated position S, in which the cannula holder (3) and the cannula (2) on the one hand and the sheath (1) on the other hand are completely separated;
- an introduction position I, in which the cannula holder (3) is just introduced into the proximal end of the sheath (1), the cannula (2) of course being within the sheath (1) and the bosses (30, 30') of the cannula holder (3) being positioned in the grooves of the receiving means (10);
- a completely retracted position R, in which the cannula holder (3) and the cannula (2) are completely inside said sheath (1), this position having three variants:
  1-a retracted pre-use position RPU comprising first and second transversely spaced sections (16a, 16b), the first section having a distal end in which the cannula holder (3) and the cannula (2) are temporarily locked by preliminary locking means (6); in this position, the cannula holder (3) is in distal longitudinal abuttal, that is to say that the lugs (30, 30'), butting against a distal wall 16c of the first section (16a), prevent the cannula holder (3) from going transversely or distally further toward the distal end of the sheath (1);

2-a retracted use position RU, in which the cannula holder (3) and the cannula (2) are inside the sheath (1), but the cannula holder (3) is not blocked longitudinally;

3-a retracted post-use position RAU, in which the cannula holder (3) and the cannula (2) are inside the sheath (1), permanently locked by final locking means (9); in this position, the cannula holder (3) can no longer be moved, either forward or rearward, with respect to the sheath (1);

an ejection position E, in which the cannula holder (3) is substantially at the distal end of the sheath (1) and in which the cannula (2) protrudes substantially completely outside said sheath (1). This ejection position E is possible only after moving into the retracted use position RU and is no longer possible after moving into the retracted post-use position RAU.

It is important to note that the positions S and I are important to "activate" the injection unit according to the invention, that is to say to prepare it so that it can be used, but that these positions are preferably not visible to the end user. In other words, the injection unit is preferably directly marketed with the cannula holder (3) and the cannula (2) in the retracted pre-use position RPU.

In order to move from one position to the other, the sheath (1) comprises, as illustrated in FIG. 8:

primary transmission means (11) (FIG. 9) for moving the cannula holder and the cannula from the introduction position I to the retracted pre-use position RPU;

secondary transition means (12) (FIG. 10) for moving the cannula holder and the cannula from the second section 16b of the hole (16) to the retracted use position RU;

guide means (14) for moving the cannula holder and the cannula from the retracted use position RU to the ejection position E, and vice versa, as many times as desired;

tertiary transition means (13) (FIG. 11) for moving the cannula holder and the cannula from the retracted use position RU to the retracted post-use position RAU;

final locking means (9) enabling said cannula holder (3) to be permanently locked in a retracted post-use position RAU.

The guide means (14) are formed, for example, by two longitudinal slots which are parallel to one another and to the axis X, these two slots preferably opening out onto the inner face (23) of the sheath (1), but not onto the outer face (24), so as to obtain a reinforcement by virtue of the material which is in the bottom of the slots and thereby to form grooves; however, it is possible to produce the slots opening out onto both the inner (23) and outer (24) faces of the sheath (1).

The sheath (1) additionally comprises a distal stop positioned at the distal end of the guide means (14). This stop is formed by the distal end of the slot constituting the guide means (14) and/or by the return of the sheath wall toward the inside of the sheath at its distal end.

The primary (11), secondary (12) and tertiary (13) transition means are preferably single-transition means, that is to say that they allow only one transition or only one movement from a preceding position toward a subsequent position and do not allow the transition or the movement in the other direction, that is to say a return to the preceding position.

In the example illustrated in FIGS. 8 to 11, these primary (11), secondary (12) and tertiary (13) transition means are each formed, on each side with respect to the axis X, by a transition portion having, in longitudinal section:

a recess (15) made in the inner face (23) of said sheath (1) and opening only onto the inner face (23) of the sheath (1)

said transition means having at each of its ends a hole (10, 16, 16', 16") opening onto the inner (23) and outer (24) faces of the sheath (1), and between these holes (10, 16, 16', 16"), an inwardly inclined flat section (17, 17a, 17b) progressively taking the depth p of said recess (15) toward a zero value.

Figure 9:
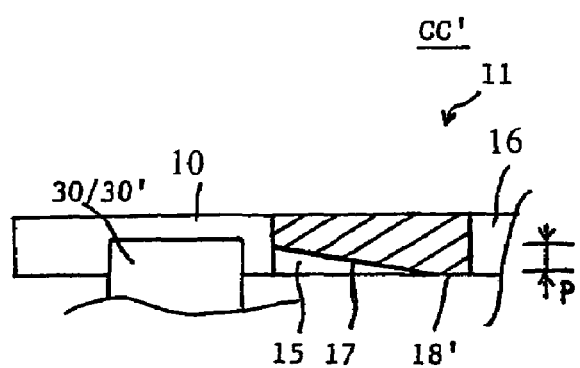
FIG. 9 illustrates a view in longitudinal section taken along CC' of FIG. 8.

In a variant, as illustrated in FIG. 9 with regard to the primary transition means (11), said transition portion additionally comprises, in longitudinal section, a straight flat section (18'), substantially parallel to the axis X, between the inclined flat section (17) and the hole (16).

In a variant, as illustrated in FIG. 10 with regard to the secondary transition means (12), said transition portion additionally comprises, in longitudinal section, two respective straight flat sections (18, 18'), substantially parallel to the axis X, between the hole (16) and the inclined flat section (17a) on the one hand and between the inclined flat section (17a) and the hole (16') on the other hand.

In the basic variant illustrated in FIG. 11, the transition portion of the transition means comprises only an inwardly inclined flat section (17b) between the holes (16", 16').

In all the variants, the inclined flat sections (17, 17a, 17b) have a length of around 5 mm for a depth p of around 1 mm, that is to say a gradient of around 20%±5%. A gentle gradient promotes the smooth passage from one position to another.

Each of the variants illustrated in FIGS. 9, 10 and 11 is applicable to one or other of the transition portions of the primary (11), secondary (12) or tertiary (13) transition means.

In a variant illustrated in FIGS. 13 and 14, the transition portion of the tertiary transition means (13) comprises, between the holes (16", 16'), a flat section (17b) inclined toward the inside of the sheath so as to form a pawl (20), and the hole (16") is extended, on each side of the inclined plane (17b) and over approximately a third of its length, by longitudinal slots (25, 25'). The longitudinal slots (25, 25') open onto both the inner (23) and outer (24) faces of the sheath (1) so as to give even greater flexibility to the final passing movement while offering greater resistance to the return to the position RU. In this variant, the depth p of the recess (15) thereby attains, as it were, a negative value.

This pawl (20) makes it possible to more strongly oppose the return to the preceding position, that is to say to the retracted use position. However, in order not to impede the movement of the cannula holder (3), the latter is then provided with two primary longitudinal slots (38, 38') not extending over the entire length of the cannula holder so as to provide additional locking in the retracted pre-use position RPU, supplementing the preliminary locking means (6); and with two secondary longitudinal slots (39, 39') extending over the length of the cannula holder so that the pawl (20) does not impede the crossing of the secondary transition means (12).

These two pairs of slots (38, 39), (38', 39'), which are visible in FIGS. 14 and 15, are made in the outer surface (34) of the cannula holder (3), in the vicinity of the bosses (30, 30') respectively. They have a depth which is at least equal to, or even greater than, the thickness of the pawl (20) with regard to the inner wall (23) of the sheath (1).

In the version illustrated, said preliminary locking means (6) include a lug (19) which is positioned between two holes each at the proximal end of the section (16a) of the hole (16), the hole (16) opening onto the inner (23) and outer (24) faces of the sheath (1).

This lug is configured so as to facilitate the retention of the bosses (30, 30') in the retracted pre-use position RPU, that is to say to facilitate the passing (i.e., distal) movement into the section 16a of the retracted pre-use position RPU and to yieldably oppose the proximal passing movement from the section 16a toward the retracted use position RU. To this end, the lug (19) has, at its end, a proximal inclined flat section and a distal appendage.

It is also possible to conceive of said primary (11) and/or secondary (12) and/or tertiary (13) transition means being formed in each case by a transition portion formed by a lug identical to the lug (19). The inclined flat section is then positioned on the side where it is desired to facilitate the transition movement and the appendage is then positioned on the side where it is desired to oppose a transition movement.

In the version illustrated, said final locking means (9) are formed by two diametrically opposed holes opening onto the inner (23) and outer (24) faces of the sheath (1).

The sheath (1) according to the invention preferably additionally comprises, at its proximal end, receiving means (10) enabling said cannula holder (3) to be positioned in an introduction position I. These receiving means (10) are preferably in the form of holes diametrically opposite one another with respect to the axis X, opening at least onto the inner face (23) of the sheath (1), as can be seen in FIG. 9.

In the case where the injection unit according to the invention is marketed with the cannula holder in the retracted pre-use position RPU, the primary transition means (11) will therefore be employed, either manually or using automated means, at the manufacturing site in order to move the cannula holder and the cannula from the introduction position I to the retracted pre-use position RPU by pushing the cannula holder provided with its cannula into the sheath while at the same time firmly holding the sheath.

The use of the sheath (1) will now be described in detail starting from the marketed position, i.e. the retracted pre-use position RPU. In this position, the distal end of the syringe can be clipped, or possibly screwed, into the cannula holder (3) by way of the thread formed on the inner face (33) of the cannula holder (3), since the distal wall of the hole in which the bosses are situated retains them longitudinally.

By virtue of the elasticity of the lug (19), when the bosses (30, 30') are in the retracted pre-use position RPU, it is only necessary to pull the syringe rearward—that is to say toward the proximal end of the sheath (1)—in order that the bosses (30, 30') move proximally to push the lug 19 transversely and pass from the section 16a into the common region of hole (16) shared by the primary (11) and secondary (12) transition means respectively.

In this common region of hole (16) the bosses (30, 30') are no longer able to return to the introduction position (10), since the transverse sheath wall adjacent to the flat section (18'), which is visible in FIG. 9, prevents them from doing so. Instead, the inclined wall 16d forces the bosses (30, 30') transversely into alignment with the section (16b) of the hole (16).

The operation of the secondary transmission means (12) to move the cannula holder and the cannula from the section 16b to the retracted use position RU is brought about by pushing the syringe into the sheath with one hand while firmly holding the sheath (1) with the other hand.

The guide means (14) allow passage from the retracted use position RU to the ejection position E by pushing the syringe with one hand while firmly holding the sheath (1) with the other hand, and passage from the ejection position E to the retracted use position RU by pulling on the syringe with one hand while firmly holding the sheath (1) with the other hand. All the intermediate positions are of course possible. It goes without saying that the user must leave free the space situated in front of the distal end of the sheath when he is using the guide means (14) so as not to accidentally prick someone or himself.

The operation of the tertiary transmission means (13), to move the cannula holder and the cannula from the retracted use position RU to the retracted post-use position RAU is operated by pulling on the syringe with one hand while firmly holding the sheath (1) with the other hand.

The cannula holder (3) is then permanently locked by the final locking means (9).

In order to separate the syringe from the injection unit, it is then only necessary to give a strong pull on the syringe with one hand while firmly holding the sheath (1) with the other hand, so as to disengage the cannula holder (3) from the distal end of the syringe. During this pulling movement, the two portions of the thread on the inner face (33) of the cannula holder (3) which are separated by the longitudinal slots (35, 35') move apart in order to release the distal end of the syringe.

After use, the cannula holder (3) therefore remains locked in the retracted post-use position RAU within the sheath (1), the cannula (2) being protected by the sheath (1); it is no longer possible for the cannula (2) to be brought out through one of the ends of the sheath, even by introducing the syringe once more into the sheath and attempting to clip or screw the distal end of the syringe once more onto the cannula holder (3), since the tertiary transmission means (13) oppose any movement of the cannula holder (3).

The invention is described in the foregoing by way of example. It is understood that a person skilled in the art is capable of producing various alternative forms of the invention without thereby departing from the scope of the patent.

The invention claim is:

1. A protective sheath for an injection cannula arranged on a cannula-holding support, the sheath being fittable on a syringe and comprising proximal and distal ends, the sheath forming:
    a retracted use position from which the cannula holder can be displaced, relative to the sheath, to an ejection position for exposing the cannula from the distal end of the sheath;
    a retracted post-use position into which the cannula holder may be displaced from the retracted use position, relative to the sheath, for permanently locking the cannula in a retracted state;
    a retracted pre-use position from which the cannula holder can be displaced to the retracted use position, relative to the sheath, the retracted pre-use position including first and second transversely spaced sections, the cannula holder being displaceable, to the retracted use position from a distal end of the second section, a distal end of the first section configured for locking the cannula holder against displacement to the second section in distal and lateral directions when the cannula holder is disposed adjacent the distal end of the first section, the first and second sections communicating with one another adjacent their proximal ends, requiring the cannula holder to be moved proximally relative to the sheath to become unlocked from the first section;

primary transition means enabling the cannula holder to be brought into the retracted pre-use position RPU;

secondary transition means enabling the cannula holder to be moved from the retracted pre-use position RPU to the retracted use position RU; and tertiary transition means enabling the cannula holder to be brought from the retracted use position RU to the retracted post-use position RAU;

wherein at least one of the primary and secondary tertiary transition means is formed at least by a transition portion having, in longitudinal section, a recess made in the inner face of said sheath, said single or said plural transition means having, at each of its or of their ends, a hole and, between these holes, an inclined flat section progressively taking the depth p of said recess toward a zero, or even negative, value.

2. The protection sheath according to claim 1 wherein the retracted use position and the second section of the retracted pre-use position are disposed along a first longitudinal line of the sheath, the first section of the retracted pre-use position being disposed along a second longitudinal line of the sheath; the retracted post-use position being disposed along a third longitudinal line of the sheath; the first, second and third longitudinal lines being transversely spaced from one another.

3. The protective sheath according to claim 1 wherein the first section of the retracted pre-use position is defined by a slot having a wall structure at its distal end which is arranged for distal and lateral abutment of the cannula holder.

4. The protective sheath according to claim 1 wherein the first and second sections are separated by a lug which has one end fixed adjacent the distal end of the first section and a second end elastically flexible adjacent the proximate end of the second section.

5. The protective sheath as claimed in claim 1 wherein said primary, secondary and tertiary transition means are single-transition means.

6. The protective sheath as claimed in claim 1, wherein said transition portion additionally comprises, in longitudinal section, a straight flat section between the inclined flat section and the hole.

7. A protective sheath as claimed in claim 1, comprising at its proximal end, receiving means enabling said cannula holder to be inserted therein, and guide means for guiding the cannula holder in the retracted use position, the ejection position, the retracted post-use position, and the retracted pre-use position.

8. The protective sheath as claimed in claim 7, wherein said receiving means and said guide means are formed at least by a longitudinally slot portion, opening at least onto the internal face of said sheath.

9. The protective sheath as claimed in claim 7, wherein said guide means are formed by two identical portions positioned diametrically opposite one another about a center axis of said sheath.

10. An injection unit formed by a sheath as claimed in claim 1, into which an injection needle or cannula arranged on a cannula-holding support is positioned.

11. The injection unit as claimed in claim 10, wherein said cannula holder has at least two longitudinal bosses positioned diametrically opposite one another with respect to the axis of said cannula holder.

12. A syringe comprising an injection needle or cannula, said syringe being equipped with a sheath as claimed in claim 1.

* * * * *